US008695785B2

United States Patent
Balk et al.

(10) Patent No.: US 8,695,785 B2
(45) Date of Patent: Apr. 15, 2014

(54) MULTI-TRACK HELICAL CONVEYOR

(75) Inventors: Wouter Balk, Baambrugge (NL);
Johannes Wilhelmus Broers,
Oosterblokker (NL)

(73) Assignee: Specialty Conveyor B.V., Zwaag (NL)

( * ) Notice: Subject to any disclaimer, the term of this patent is extended or adjusted under 35 U.S.C. 154(b) by 110 days.

(21) Appl. No.: 13/140,111

(22) PCT Filed: Oct. 8, 2009

(86) PCT No.: PCT/EP2009/063108
§ 371 (c)(1),
(2), (4) Date: Jun. 16, 2011

(87) PCT Pub. No.: WO2010/040809
PCT Pub. Date: Apr. 15, 2010

(65) Prior Publication Data
US 2012/0043182 A1 Feb. 23, 2012

(30) Foreign Application Priority Data

Oct. 10, 2008 (NL) .................................... 2002078

(51) Int. Cl.
*B65G 21/18* (2006.01)
(52) U.S. Cl.
USPC ........................................ 198/778; 198/347.1
(58) Field of Classification Search
USPC .................... 198/347.1, 347.2, 778
See application file for complete search history.

(56) References Cited

U.S. PATENT DOCUMENTS

| 2,271,091 A | | 1/1942 | Pecker et al. | |
| 3,664,487 A | | 5/1972 | Ballenger | |
| 4,036,352 A | * | 7/1977 | White | 198/778 |
| 5,490,589 A | * | 2/1996 | Golz et al. | 198/444 |
| 6,666,322 B2 | * | 12/2003 | Biondi et al. | 198/347.1 |
| 8,302,764 B2 | * | 11/2012 | Johnson | 198/778 |
| 2002/0195317 A1 | * | 12/2002 | Wipf | 198/602 |
| 2005/0217977 A1 | * | 10/2005 | Hartness et al. | 198/594 |
| 2006/0185962 A1 | | 8/2006 | Hartness | |
| 2011/0061993 A1 | * | 3/2011 | Seger et al. | 198/367 |
| 2011/0174596 A1 | * | 7/2011 | Johnson | 198/606 |

FOREIGN PATENT DOCUMENTS

| DE | 29624457 | 11/2003 |
| EP | 0544085 | 10/1992 |
| EP | 0738478 | 10/1996 |
| JP | 04217054 | 8/1992 |
| WO | WO 0222470 | 3/2002 |
| WO | WO2005102880 | 11/2005 |
| WO | WO2008079010 | 7/2008 |

OTHER PUBLICATIONS

Written Opinion of the European Patent Office in counterpart foreign application No. PCT/EP2009/063108 filed Oct. 8, 2009.
Official Search Report of the European Patent Office in counterpart foreign application No. PCT/EP2009/063108 filed Oct. 8, 2009.

* cited by examiner

*Primary Examiner* — James R Bidwell
(74) *Attorney, Agent, or Firm* — Steven M. Koehler; Westman, Champlin & Koehler, P.A.

(57) ABSTRACT

A conveyor for conveying products comprises at least a drivable helically-shaped inner track conveyor member and a drivable helically-shaped outer track conveyor member. The outer track conveyor member surrounds the inner track conveyor member. The pitches of the inner track conveyor member and the outer track conveyor member are different.

13 Claims, 5 Drawing Sheets

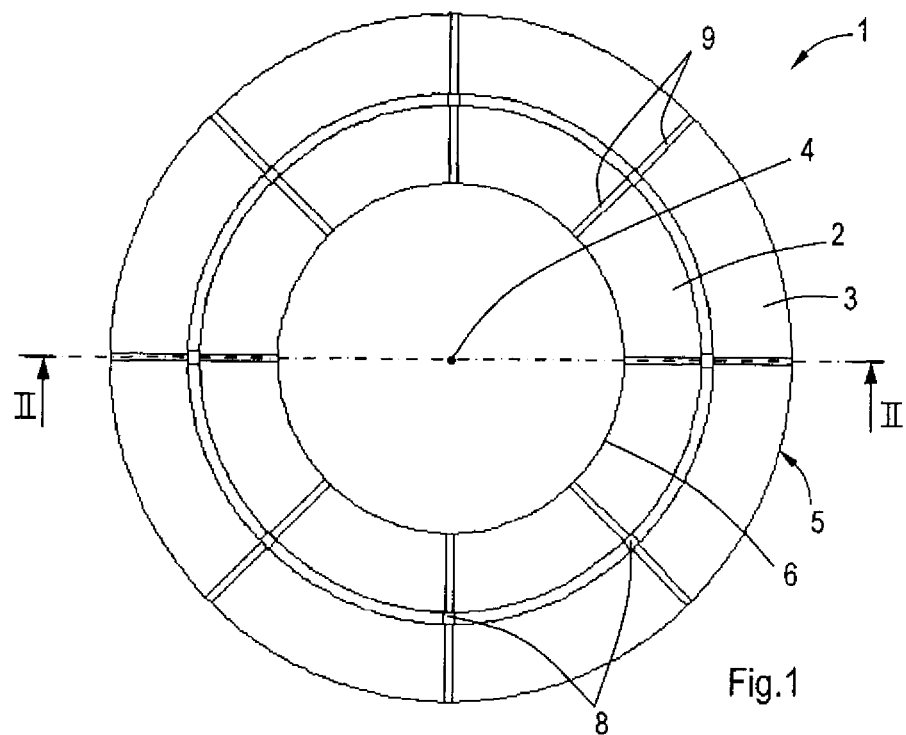
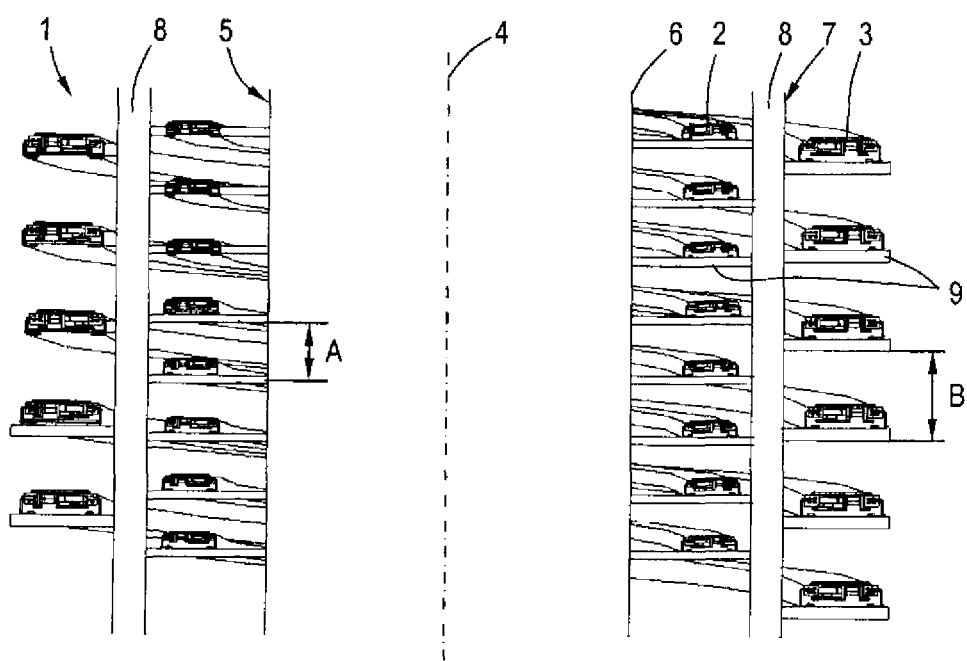
Fig.1
Fig.2

MULTI-TRACK HELICAL CONVEYOR

CROSS-REFERENCE TO RELATED APPLICATION

This application is a Section 371 National Stage Application of International Application PCT/EP2009/063108 filed Oct. 8, 2009 and published as WO 2010/040809 in English.

BACKGROUND

The discussion below is merely provided for general background information and is not intended to be used as an aid in determining the scope of the claimed subject matter.

Aspects of the present invention relate to a conveyor for conveying products, comprising at least a drivable helically-shaped inner track conveyor member and a drivable helically-shaped outer track conveyor member, wherein the outer track conveyor member surrounds the inner track conveyor member.

Such a conveyor is known from WO 2008/079010. Products which are received at inlets of the known conveyor are transported downwardly along the helically shaped inner and outer track conveyor members and leave the conveyor at different height levels. A disadvantage of the known conveyor is that the ratio between the lengths of the paths along the inner and outer track conveyor members is fixed.

SUMMARY

This Summary and the Abstract herein are provided to introduce a selection of concepts in a simplified form that are further described below in the Detailed Description. This Summary and the Abstract are not intended to identify key features or essential features of the claimed subject matter, nor are they intended to be used as an aid in determining the scope of the claimed subject matter. The claimed subject matter is not limited to implementations that solve any or all disadvantages noted in the Background.

A conveyor herein described includes pitches of the inner track conveyor member and the outer track conveyor member that are different. This feature provides the opportunity to vary the ratio between the path lengths of the inner and outer track conveyor members. In traditional conveyors the pitches of the helically-shaped inner track conveyor member and the helically-shaped outer track conveyor member are the same in order to support the inner and outer track conveyor members at the same height levels. As a consequence, as seen along a certain distance along the center line of the conveyor the distance along the inner track conveyor member is shorter than that of the outer track conveyor member due to the smaller diameter of the inner track conveyor member with respect to the outer track conveyor member. Due to different pitches of the conveyor the distance along the path of the inner track conveyor member may even be the same as the distance along the path of the outer track conveyor member as measured over a certain distance along the center line of the conveyor. This means that the inclination along the inner track conveyor member is steeper than that of the outer track conveyor member. In contrast to this, the maximum allowable inclination of the inner track conveyor member of traditional conveyors determined the inclination of the outer track conveyor member, as well.

The pitch of the outer track conveyor member may be larger than that of the inner track conveyor member in order to bring the path lengths of the inner track conveyor member and the outer track conveyor member, as measured between two parallel planes extending perpendicularly to a longitudinal center line of the conveyor, closer to each other.

In a particular embodiment the pitches of the inner and outer track conveyor members are selected such that the lengths along the paths of the inner and outer track conveyor members are substantially the same as measured between two parallel planes extending perpendicularly to a longitudinal center line of the conveyor.

In an alternative embodiment the inclination along the helical path of the inner track conveyor member is substantially the same as that of the outer track conveyor member.

The inner track conveyor member and the outer track conveyor member may be supported by supporting members which are fixed to at least a frame supporting element extending substantially parallel to a longitudinal center line of the conveyor and disposed between the inner and outer track conveyor members. In this case the supporting elements support both the inner and outer track conveyor members, which means efficient use of space. Moreover, traditional conveyors such as described in respect of the prior art conveyor hereinbefore comprise a central column from which elongated supporting members project in outward direction; traditionally, in case of adding a parallel helical track such an elongated supporting member could be extended to support the outer track conveyor member, as well. In case of different pitches elongated supporting members projecting from a central column could be applied for supporting the outer track conveyor member, but this may be disadvantageous because the supporting members would be located within the space between two height levels of the inner track conveyor member.

The helical shape of the inner track conveyor member and/or the outer track conveyor member may have a clockwise turning or anti-clockwise turning orientation, as seen parallel to a longitudinal center line of the conveyor. This provides, for example, freedom of positioning an inlet and outlet for the inner and outer track conveyor members.

In one embodiment the inner track conveyor member and the outer track conveyor member are coupled to each other such that products transported by the conveyor are transported both along the path of the inner track conveyor member and the outer track conveyor member. In this embodiment the products are transported upwardly via the inner track conveyor member and downwardly via the outer track conveyor member or in opposite direction. In fact the inner track conveyor member and the outer track conveyor member can be integrated in a single conveyor member which follows the entire conveyor under operating conditions.

An aspect of the invention is also related to a conveyor for conveying products, comprising at least a helically-shaped inner track conveyor member and a helically-shaped outer track conveyor member, wherein the inner track conveyor member is surrounded by the outer track conveyor member, wherein the inner and outer track conveyor members are drivable by driving means which follow the paths of the inner and outer track conveyor members, wherein the inner track conveyor member and/or the outer track conveyor member is/are supported by at least a frame supporting element extending substantially parallel to a longitudinal center line of the conveyor and disposed between the inner and outer track conveyor members.

An aspect of the invention is also related to a conveyor for conveying products, comprising at least a helically-shaped inner track conveyor member and a helically-shaped outer track conveyor member, wherein the inner track conveyor member is surrounded by the outer track conveyor member, wherein the inner and outer track conveyor members are drivable by driving means which follow the paths of the inner and outer track conveyor members, wherein the inner track conveyor member is supported by at least a frame supporting element extending substantially parallel to a longitudinal center line of the conveyor and disposed at an inner circumferential side of the inner track conveyor member.

An aspect of the invention is also related to a conveyor for conveying products, comprising at least a helically-shaped inner track conveyor member and a helically-shaped outer track conveyor member, wherein the inner track conveyor member is surrounded by the outer track conveyor member, wherein the inner and outer track conveyor members are drivable by driving means which follow the paths of the inner and outer track conveyor members, wherein the outer track conveyor member is supported by at least a frame supporting element extending substantially parallel to a longitudinal center line of the conveyor and disposed at an outer circumferential side of the outer track conveyor member.

The frame supporting element may comprises a plurality of pillar-shaped elements extending substantially parallel to each other.

The inner track conveyor member and the outer track conveyor member may each be drivable by a driving belt, e.g. a chain, which follows the helical path of the inner track conveyor member and the outer track conveyor member. The driving belt may be guided at least radially by a stationary frame of the conveyor.

BRIEF DESCRIPTION OF THE DRAWINGS

Aspects of the invention will hereafter be elucidated with reference to the schematic drawings showing embodiments of the invention by way of example.

FIG. 1 is a sectional view of an embodiment of the conveyor.

FIG. 2 is a cross-sectional view along the line II-II of FIG. 1 on a larger scale.

DETAILED DESCRIPTION OF THE ILLUSTRATIVE EMBODIMENTS

Figure 3:
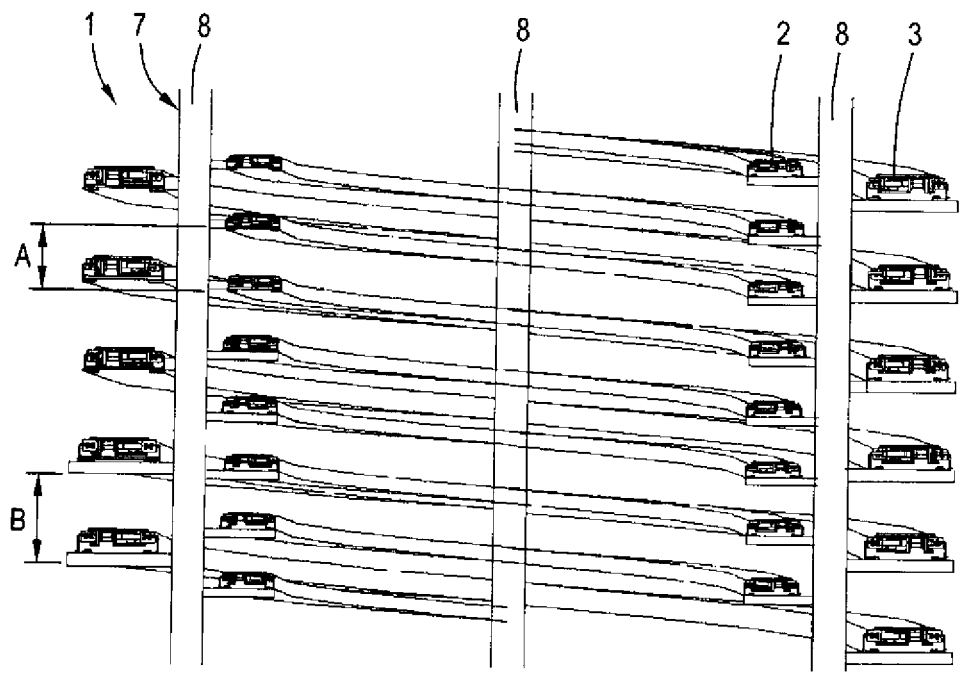
FIG. 3 is a similar view as FIG. 2 on a larger scale, but showing an alternative embodiment.

FIGS. 1 and 2 show different views of an embodiment of a conveyor 1 for conveying products. The conveyor 1 comprises a drivable helically-shaped inner track conveyor member 2 and a drivable helically-shaped outer track conveyor member 3. The outer track conveyor member 3 surrounds the inner track conveyor member 2, as seen from above in FIG. 1, and the conveyor 1 has a longitudinal center line 4, which is both the longitudinal center line of the inner track conveyor member 2 and the outer track conveyor member 3. Thus, in this embodiment the longitudinal center lines of the inner track conveyor member 2 and the outer track conveyor member 3 substantially coincide. As can be seen in FIG. 1 the cross sections of both the inner and outer track conveyor members 2, 3 are circular.

FIG. 2 shows that the pitch of the inner track conveyor member 2 is smaller than that of the outer track conveyor member 3. The pitch of the inner track conveyor member 2 is indicated by A and the pitch of the outer track conveyor member 3 is indicated by B. In a particular embodiment the pitches A, B of the inner and outer track conveyor members 2, 3 may be selected such that the path lengths along the inner and outer track conveyor members 2, 3 are substantially the same as measured between two parallel planes extending perpendicularly to the longitudinal center line 4 of the conveyor 1.

The embodiment of FIGS. 1 and 2 comprises a frame 5, which is provided with a central pipe or column 6 extending parallel to the longitudinal center line 4. The frame 5 is further provided with a frame support 7 comprising eight pillars 8 extending substantially parallel to the longitudinal center line 4 of the conveyor 1 at a predetermined angular distance with respect to each other and being disposed between the inner track conveyor member 2 and the outer track conveyor member 3. The frame support 7 comprises supporting members 9 by which the inner track conveyor member 2 and the outer track conveyor member 3 are supported. FIG. 2 shows that the supporting members 9 associated with the inner track conveyor member 2 are not always aligned with the supporting member 9 associated with the outer track conveyor member 2 as seen in radial direction from the center line 4. This is a consequence of the different pitches A, B of the inner and outer track conveyor members 2, 3.

Alternatively, the frame support 7 could be replaced by supporting members 9 which are vertically staggered. This means that both the inner track conveyor member 2 and the outer track conveyor member 3 are supported by supporting members 9 which are fixed to the central column 6.

FIG. 3 shows an alternative embodiment of the conveyor 1. In this case the central column 6 of the embodiment of FIGS. 1 and 2 is eliminated and the frame support 7 comprises four pillars 8 extending substantially parallel to the longitudinal center line 4 of the conveyor 1 and being disposed between the inner track conveyor member 2 and the outer track conveyor member 3.

Figure 4:
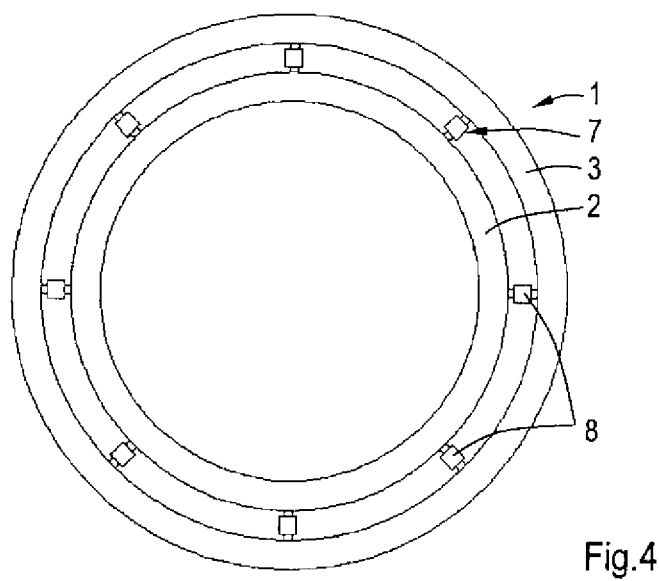
FIG. 4 is a plan view of another alternative embodiment of the conveyor.

FIG. 4 shows another alternative embodiment of the conveyor 1. In this case the frame support 7 comprises eight pillars 8 as frame supporting elements extending substantially parallel to the longitudinal center line 4 of the conveyor 1 and being disposed between the inner track conveyor member 2 and the outer track conveyor member 3. The difference of this embodiment with respect to that of FIG. 1 is that the column 6 is eliminated.

Figure 5A:
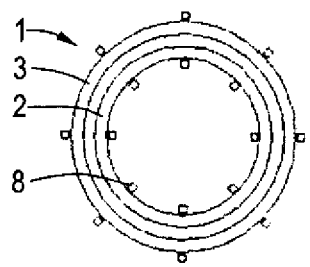
FIGS. 5a-e are similar views as FIG. 4 on a smaller scale, showing other alternative embodiments.
Figure 5B:
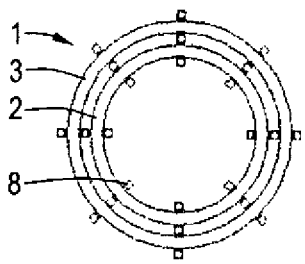
Figure 5C:
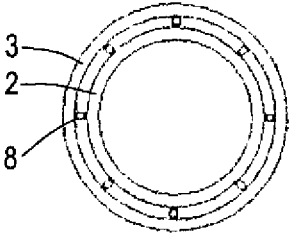
Figure 5D:
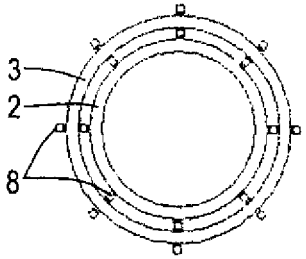
Figure 5E:
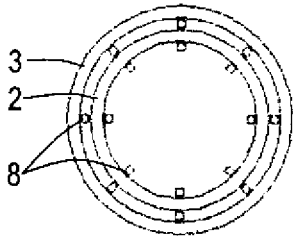

FIG. 5a-5e show different alternative embodiments, wherein the embodiment of FIG. 5c is analogous to that of FIG. 4. In FIG. 5a, b, e the inner track conveyor member 2 is supported by pillars 8 extending substantially parallel to the longitudinal center line 4 of the conveyor 1 and disposed at an inner circumferential side of the inner track conveyor member 2. FIG. 5a, 5b, 5d show that the outer track conveyor member 3 is supported by pillars 8 extending substantially parallel to a longitudinal center line of the conveyor and disposed at an outer circumferential side of the outer track conveyor member. FIG. 5b-e show embodiments in which the inner track conveyor member 2 is supported by pillars extending substantially parallel to the longitudinal center line 4 of the conveyor 1 and disposed at an inner circumferential side of the outer track conveyor member 3.

Figure 6:
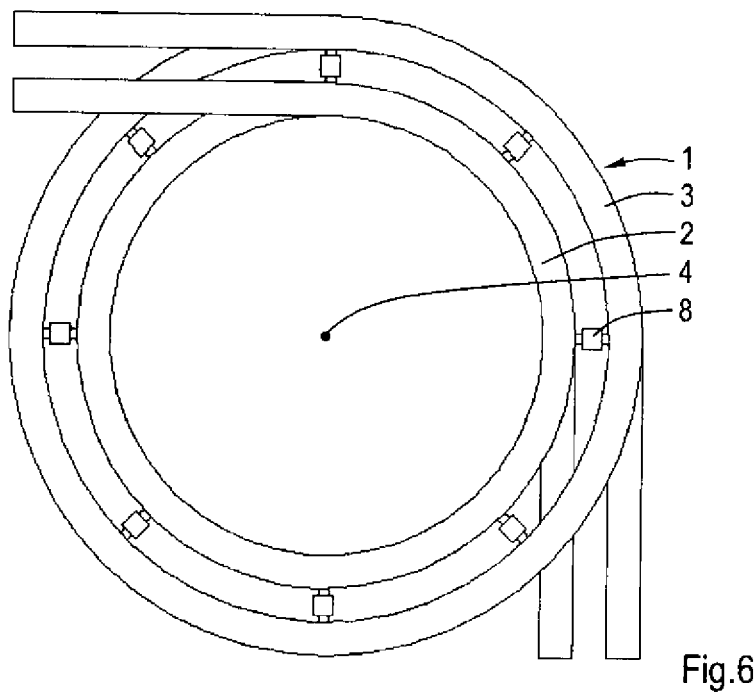
FIGS. 6-8 are plan views of different alternative embodiments of the conveyor.

FIG. 6 shows a plan view of an alternative embodiment of a conveyor 1 which comprises an inner track conveyor member 2 and an outer track conveyor member 3. Each of the conveyor members 2, 3 has its own inlet and outlet and both conveyor members 2, 3 extend more or less parallel to each other. The conveyor 1 may be adapted such that products on both conveyor members 2, 3 are transported in the same direction or in opposite direction. In the latter case, the products will be transported upwardly by the one conveyor member 2 and downwardly by the other conveyor member 3. The pitches of the conveyor members 2, 3 may be different such that the distance of the path that the products follow on the outer track conveyor member 3 is not automatically longer than the path that the products follow on the inner track conveyor member 2.

Figure 7:
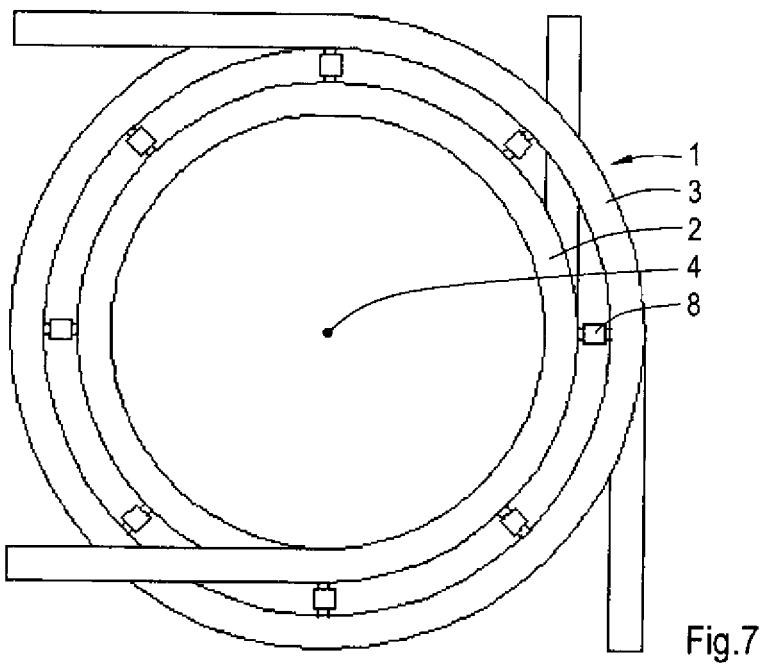

FIG. 7 shows an embodiment of the conveyor 1 of which the helical shapes of the inner and outer conveyor members 2, 3 have different helical orientations. As seen in a direction parallel to the longitudinal center line 4 one of the conveyor members 2 has an anti-clockwise turning orientation whereas the other conveyor member 3 has a clockwise turning orientation.

Figure 8:
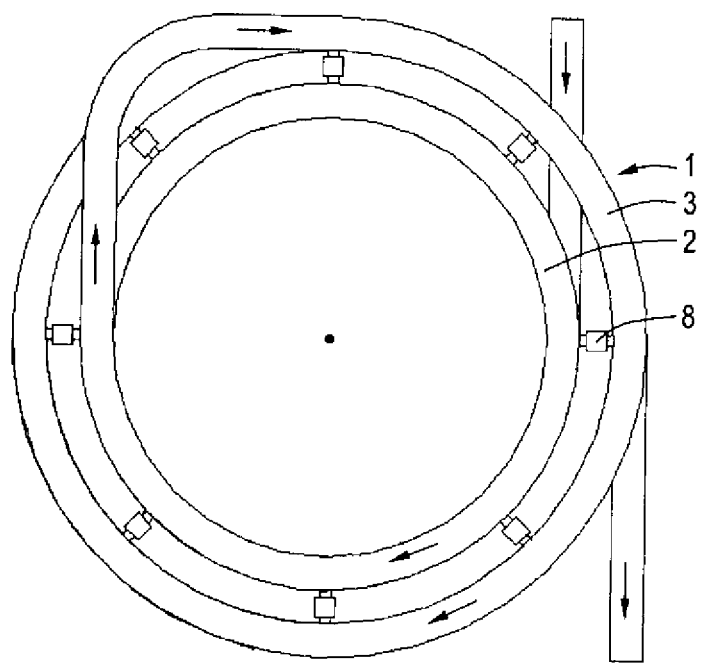

The helical shapes of the conveyor members 2, 3 of the embodiment as shown in FIG. 8 have the same orientations as those in FIG. 7, but in this case the inner and outer conveyor members 2, 3 are coupled to each other such that products follow the inner track conveyor member 2 upwardly and the outer track conveyor member 3 downwardly or in the opposite direction. In this case a single drivable conveyor belt may be applied whereas in the other embodiments as described hereinbefore separately drivable conveyor belts may be applied.

The inner and outer conveyor members 2, 3 may comprise conveyor belts or slats which are connected to a driven chain.

From the foregoing, it will be clear that at least some aspects of the invention provide a conveyor comprising at least a drivable helically-shaped inner track conveyor member and a drivable helically-shaped outer track conveyor member of which the path lengths can be varied.

The invention is not limited to the embodiments shown in the drawings and described hereinbefore, which may be varied in different manners within the scope of the claims and their technical equivalents. It is possible, for example, that the cross section of the conveyor is not circular, but an alternative shape, for example elliptical. Furthermore, the embodiments as shown hereinbefore may be combined, for example variations in pitch, supporting frame structure or the like.

The invention claimed is:

1. A conveyor for conveying products, comprising at least a drivable helically-shaped inner track conveyor member and a drivable helically-shaped outer track conveyor member, wherein the outer track conveyor member surrounds the inner track conveyor member wherein the pitches (A, B) of the inner track conveyor member and the outer track conveyor member are different between two parallel planes extending perpendicularly to a longitudinal center line of the conveyor within which both the inner and outer truck conveyor members follow helical paths.

2. The conveyor according to claim 1, wherein the pitch (B) of the outer track conveyor member is larger than that of the inner track conveyor member.

3. The conveyor according to claim 2, wherein the pitches (A, B) of the inner and outer track conveyor members are selected such that the lengths along the paths of the inner and outer track conveyor members are substantially the same as measured between two parallel planes extending perpendicularly to the longitudinal center line of the conveyor.

4. The conveyor according to claim 1, wherein the inclination along the helical path of the inner track conveyor member is substantially the same as that of the outer track conveyor member.

5. The conveyor according to claim 1, wherein the inner track conveyor member and the outer track conveyor member are supported by supporting members which are fixed to at least a frame supporting element extending substantially parallel to the longitudinal center line of the conveyor and disposed between the inner and outer track conveyor members.

6. The conveyor according to claim 1, wherein the helical shape of the inner track conveyor member and/or the outer track conveyor member has/have a clockwise turning or anti-clockwise turning orientation, as seen parallel to the longitudinal center line of the conveyor.

7. The conveyor according to claim 1, wherein the inner track conveyor member and the outer track conveyor member are coupled to each other such that products transported by the conveyor are transported both along the path of the inner track conveyor member and the outer track conveyor member.

8. A conveyor for conveying products according to claim 1, wherein the inner and outer track conveyor members are drivable by a driving member configured to follow the paths of the inner and outer track conveyor members, wherein the inner track conveyor member and/or the outer track conveyor member is/are both supported by at least a frame supporting element extending substantially parallel to the longitudinal center line of the conveyor and disposed between the inner and outer track conveyor members.

9. A conveyor for conveying products according to claim 1, wherein the inner and outer track conveyor members are drivable by a driving member configured to follow the paths of the inner and outer track conveyor members, wherein the inner track conveyor member is supported by at least a frame supporting element extending substantially parallel to the longitudinal center line of the conveyor and disposed at an inner circumferential side of the inner track conveyor member.

10. The conveyor according to claim 8 wherein the inner track conveyor member is supported by at least a frame supporting element extending substantially parallel to the longitudinal center line of the conveyor and disposed at an inner circumferential side of the inner track conveyor member.

11. The conveyor according to claim 8, wherein the frame supporting element comprises a plurality of pillar-shaped elements extending substantially parallel to each other.

12. The conveyor according to claim 8, wherein the inner track conveyor member and the outer track conveyor member are each drivable by a driving belt which follows the helical paths of the inner track conveyor member and the outer track conveyor member.

13. A conveyor according to claim 1, wherein the conveyor is adapted such that the inner track conveyor member and the outer track conveyor member are drivable in the same upward or downward direction of a helix.

* * * * *